United States Patent [19]

Abel, Jr.

[11] Patent Number: 4,693,715
[45] Date of Patent: Sep. 15, 1987

[54] ARTIFICIAL CORNEA

[76] Inventor: Robert Abel, Jr., 1100 North Grant Ave., Wilmington, Del. 19805-2695

[21] Appl. No.: 876,177

[22] Filed: Jun. 19, 1986

[51] Int. Cl.⁴ .............................................. A61F 2/14
[52] U.S. Cl. ..................................................... 623/5
[58] Field of Search ........................................ 623/4-6

[56] References Cited

U.S. PATENT DOCUMENTS

| | | |
|---|---|---|
| 2,517,523 | 4/1949 | Batchelder . |
| 2,714,721 | 8/1955 | Stone, Jr. . |
| 2,754,520 | 7/1956 | Crawford, Jr. . |
| 2,952,023 | 9/1960 | Rosen . |
| 3,228,741 | 1/1966 | Becker ............................... 623/4 X |
| 3,454,966 | 7/1969 | Rosen ................................... 623/4 |
| 3,458,870 | 8/1969 | Stone, Jr. . |
| 3,945,054 | 3/1976 | Fedorov et al. . |
| 4,126,904 | 11/1978 | Shepard . |
| 4,346,482 | 8/1982 | Tennant et al. . |
| 4,402,579 | 9/1983 | Poler ................................... 623/6 X |
| 4,470,159 | 9/1984 | Peyman . |

FOREIGN PATENT DOCUMENTS

| | | | |
|---|---|---|---|
| 2081469A | 2/1982 | United Kingdom .................... | 623/5 |
| 562277 | 8/1977 | U.S.S.R. .................................. | 623/5 |

OTHER PUBLICATIONS

The Leiske Physioflex Style 10 Anterior Chamber Lens (Advertisement Brochure), Surgidev Corp., 1421 State St., Santa Barbara, CA. 93101, 1981.
Hernando Cardona, Keratoprosthesis, American Journal of Opthalmology, vol. 54, pp. 287-294, (1962).

Primary Examiner—Ronald L. Frinks
Attorney, Agent, or Firm—Roylance, Abrams, Berdo & Goodman

[57] ABSTRACT

A corneal implant for replacing injured or opaque portions of a natural cornea. The implant comprises a substantially circular main body portion having anterior and posterior surfaces and a radially outwardly facing, substantially cylindrical peripheral surface. Means are provided on the main body portion for receiving sutures therethrough to securely couple the main body portion to the cornea. The peripheral surface has a height H greater than the thickness T of the corneal aperture so that when the corneal implant is sutured into place in a surgically created corneal aperture, the peripheral surface will extend posterior of the cornea to prevent the corneal membrane from growing over the posterior surface of the implant. The corneal implant can be easily attached by simple surgical techniques. First, the opaque or injured portions of the cornea are excised to provide a substantially circular corneal aperture. The corneal implant is then positioned with the periheral surface engaging the edge forming the corneal aperture and sutured into place.

26 Claims, 4 Drawing Figures

ARTIFICIAL CORNEA

FIELD OF THE INVENTION

This invention relates to a corneal implant adapted to be received in a substantially circular corneal aperture and sutured thereto.

BACKGROUND OF THE INVENTION

For many years, ophthalmologists have used keratoprosthetic implants in an attempt to restore vision to patients whose corneas have been injured or become opaque. Their attempts are well documented by patents and other publications. For example, U.S. Pat. Nos. 2,517,523 to Batchelder, 2,714,721 and 3,458,870 to Stone, Jr., 2,754,520 to Crawford, Jr., 2,952,023 and 3,454,966 to Rosen, 3,945,054 to Fedorov et al., and 4,470,159 to Peyman each disclose keratoprosthetic implants. These implants are generally classified by their relationship to the surrounding corneal tissue.

The Stone, Jr., Fedorov et al., and Peyman patents disclose implants designed to be inserted between surgically established corneal layers and anchored in place by the ingrowth of the stroma. Some of these also include removeable lens elements coupled to the anterior chamber supporting means that it anchored between the corneal layers. For a general review of intralamellar keratoprostheses, see Cardona, "Keratoprosthesis", *American Journal of Ophthalmology*, Vol. 54, 284-294 (1962).

The Rosen patents disclose two-part implants comprising a retaining ring secured to the corneal rim and a transparent plastic member that is secured to the retaining ring.

Crawford, Jr. discloses an implant having upper and lower flanges. After a circular portion of the cornea is removed, the implant is inserted and rotated until the corneal rim is engaged in the recess defined by the flanges.

Each of the above implants, however, has one or more associated drawbacks. The Stone, Jr., Fedorov et al., and Peyman implants require the difficult surgical procedure of surgically establishing corneal layers and thereafter inserting a prosthesis between the layers. The Rosen implants require the surgeon to first attach a retaining ring and thereafter attach a lens to the retaining ring. The Crawford, Jr. implant requires a surgeon to make a first surgical cut to remove a circular piece of the cornea, and a second surgical cut to facilitate introduction of the implant into the circular opening. the surgeon must then delicately position and rotate the implant until it is correctly seated on the corneal rim. Another drawback of many corneal implants is the tendency for the corneal membrane tissue to overgrow the posterior portion of the prosthesis, thereby interfering with light perception and altering light projection.

Alternatively, the damaged cornea can be replaced with a human donor cornea. However, this procedure also has numerous associated drawbacks. The patient can have an adverse reaction to the donor cornea tissue, or the donor cornea itself can deteriorate from aging or ulceration. However, themost common postoperative complication from using donor corneas is the development of corneal astigmatism, i.e., defective vision resulting from a lack of symmetry in the cornea. This is often caused by deformation of the donor cornea from the pull of the sutures used to attach the donor cornea to the patient's cornea. Additionally, there is a chronic shortage of donor corneas.

Thus, there is a continuing need for a corneal implant that (1) can be attached using only simple surgical techniques, (2) can prevent the growth of corneal membrane over the posterior portion of the implant, (3) does not adversely react with the patient's cornea, (4) does not deteriorate from aging or ulceration, (5) prevents astigmatism resulting from deformation caused by the pull of sutures, and (6) is available in an abundant supply.

SUMMARY OF THE INVENTION

Accordingly, it is an object of the invention to provide a corneal implant which can be attached using only simple surgical techniques.

Another object of this invention is to provide a corneal implant that can prevent the growth of corneal membrane over the posterior portion of the implant.

Another object of the invention is to provide a corneal implant that does not adversely react with the patient's cornea.

Another object of this invention is to provide a corneal implant that does not deteriorate from aging or ulceration.

Another object of this invention is to provide a corneal implant that prevents astigmatism resulting from deformation caused by the pull of sutures.

Yet another object of this invention is to provide a corneal implant that is available in abundant supply.

The foregoing objects are basically attained by a corneal implant adapted to be received in a substantially circular corneal aperture and sutured thereto, the cornea having a thickness T, comprising a substantially circular main body portion having anterior and posterior surfaces, the main body portion having a radially outwardly facing, substantially cylindrical peripheral surface with a height greater H than T and adapted to engage the edge forming the corneal aperture; and means on the main body portion for receiving sutures therethrough to couple the main body portion to the cornea, the peripheral surface extending posterior of the cornea when the implant is sutured to the cornea.

Other objects, advantages, and salient features of the present invention will become apparent from the following detailed description, which, taken in conjunction with the annexed drawings, discloses a preferred embodiment of the invention.

BRIEF DESCRIPTION OF THE DRAWINGS

Referring now to the drawings which form a part of this original disclosure.

DETAILED DESCRIPTION OF THE INVENTION

Figure 1:
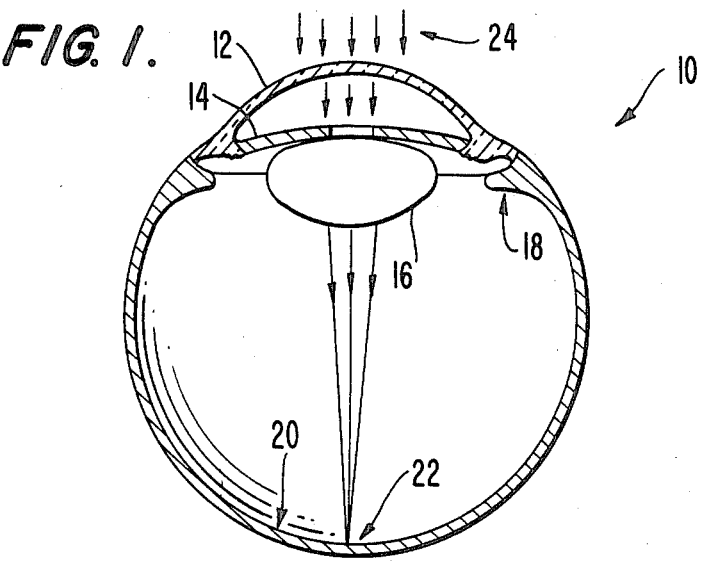
FIG. 1 is a side elevational view in longitudinal section of a schematic representation of a human eye including a natural cornea.

As seen in FIG. 1, an eye 10 is shown including the cornea 12, iris 14, lens 16, the ciliary sulcus 18 adjacent to the lens, the retina 20 and the macula 22.

As illustrated in FIG. 1, light rays 24 pass through the cornea 12 and are focused directly on the macula 22 by means of the cornea 12 and the lens 16, thereby providing focused vision. However, when portions of the cornea are injured or become opaque, the light rays 24 are not properly focused by the cornea nor properly transmitted through the cornea to the lens, the vision is markedly diminished.

Figure 2:
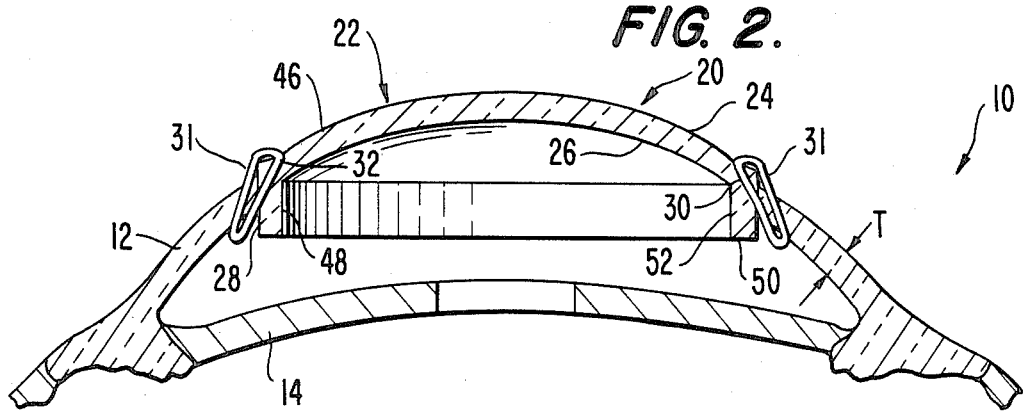
FIG. 2 is a side elevational view in longitudinal section similar to that shown in FIG. 1 except that a substantially circular portion of the cornea has been removed and replaced with a corneal implant in accordance with the invention.
Figure 4:
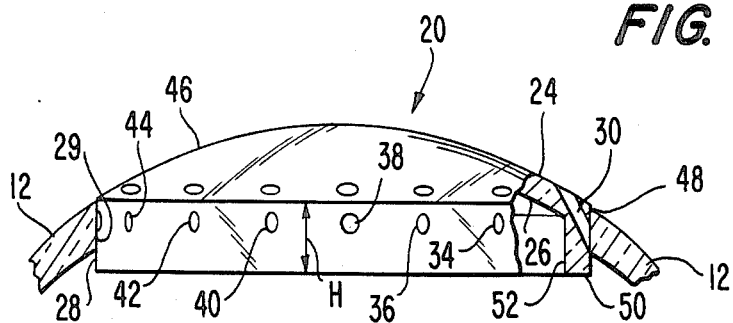
FIG. 4 is a perspective view of the corneal implant shown in FIGS. 2-3.
Figure 3:
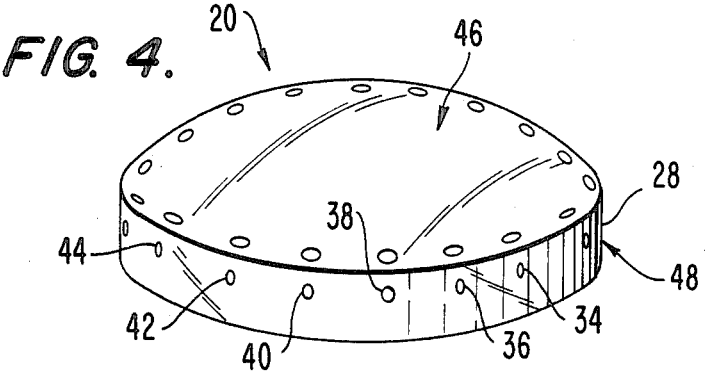
FIG. 3 is a side elevational view in partial section of the corneal implant shown in FIG. 2.

Accordingly, the present invention as seen in FIGS. 2–4 comprises replacing a substantially circular portion of the natural cornea 12 with a corneal implant 20 in accordance with the invention so that light rays are properly transmitted through and focused by the corneal implant and subsequently focused onto the macula 22.

As seen in FIGS. 2–4, corneal implant 20 comprises a substantially circular main body portion 22 having an anterior surface 24, a posterior surface 26, and a radially outwardly facing, substantially smooth cylindrical peripheral surface 28 engaging the circular edge 29 forming the corneal aperture. The peripheral surface 28 has a height H greater than the thickness T of the cornea 12. The corneal implant 20 also includes means for receiving sutures 31 therethrough to couple the main body portion to the cornea. The means are shown as throughbores 30, 32, 34, 36, 38, 40, 42 and 44. When the implant 20 is sutured into place in the corneal aperture, the peripheral surface 28 extends posterior of the cornea, thereby preventing growth of the corneal membrane over the posterior surface of the implant.

Preferably, the main body portion 22 comprises a convex portion 46 and an annular ridge portion 48 extending posterior of the convex portion 46. The annular ridge portion 48 includes an annular posterior surface 50 and a radially inwardly facing substantially cylindrical surface 52. The annular posterior surface 50 can be flat as shown or alternatively can be rounded or angled to increase the prevention of overgrowth of tissue by the corneal membrane.

The means for receiving sutures is shown as throughbores, but can be any means that is capable of receiving sutures therethrough for the purpose of securely coupling the main body portion to the cornea. Generally such means will comprise openings or apertures such as throughbores having a diameter sufficiently large to accommodate the suture. While throughbores are preferred because they simplify the surgical process, other means are contemplated. For example, certain areas of the implant can be comprised of a material that can be easily penetrated by a needle and suture. When the means used are throughbores, as shown in FIGS. 2–4, the implant will generally require from about 12 to about 24 such throughbores, preferably equally circumferentially spaced about the main body portion.

The implant 20 can be any size suitable for insertion into a corneal aperture. Generally, the main body portion can have a diameter of from about 5 mm. to about 10 mm., and an overall height of up to about 2.0 mm. If the implant height is much greater, the peripheral surface 28 might extend so far into the anterior chamber that it could inadvertently scratch the patient's iris when he rubs his eye. The height H of the peripheral surface 28 should generally exceed the thickness T of the patient's cornea by from about 0.1 mm. to about 0.5 mm. Since the thickness of a patient's cornea at its periphery is usually about 1.0 mm., the height of the peripheral surface 28 will usually be from about 1.1 mm. to about 1.5 mm. This will prevent corneal membrane tissue from growing over the posterior surface of the implant. The thickness of the material comprising the implant can generally range from about 0.1 mm. to about 1.5 mm.

Normally, the anterior surface 24 of the main body portion 22 is convex, and the posterior surface 26 is concave, thereby approximating the general configuration of the excised natural cornea. Alternatively, the posterior surface can be flat, i.e., planar. Another alternative is to shape the implant to correct any refractive errors of the eye such as myopia or hyperopia.

The implant can comprise any hard or soft synthetic material that is (1) compatible with the patient's corneal tissue, (2) sufficiently rigid to prevent deformation by the pull of sutures, (3) resistant to degeneration, and (4) permeable to gases such as oxygen and carbon dioxide. The pore size, however, should be sufficiently small to prevent bacteria from entering the eye. Exemplary synthetic materials that can be used include methacrylate, silicone, polymethyl methacrylate, hydroxyethyl methacrylate, lower alkyl butyrates, a silicone-acrylate copolymer, a fluorocarbon such as Teflon, polypropylene, polyethylene terephthalate, GoreTex, which is a tradename for stretched polytetrafluoroethylene having approximately nine billion randomly spaced microscopic pores per square inch, each pore being 20,000 times smaller than a water drop but 700 times larger than a water vapor molecule and is manufactured by W.L. Gore & Associates, 3 Blue Ball Road, Elkton, Maryland or a combination of the above polymeric materials.

The implant can also include an ultraviolet chromophore to prevent degeneration of the implant from UV light and to protect the internal areas of the eye against UV toxicity.

The implant can be integrally formed or it can be comprised of separate sections, e.g., a convex portion and an annular ridge portion, that are coupled together in any suitable manner, such as adhesive bonding.

The implant of this invention can be attached using very simple and conventional surgical techniques. First, the injured or opaque areas of the natural cornea are excised to provide a centrally located, substantially circular corneal aperture as in conventional penetrating keratoplasty. The implant is then placed into the corneal aperture with the peripheral surface engaging the edge forming the corneal aperture. The implant can be held stationary for suturing by, for example, injecting viscoelastic materials or air bubbles into the anterior chamber or by skewering the peripheral cornea with fine wires prior to excising the damaged area, thereby providing supporting wires for the implant. Permanent suture such as polypropylene or Mersilene (a polyester fiber suture produced by Ethicon) should be used. Routine nylon sutures should be avoided because of their tendency toward ultimate biodegradation.

While one advantageous embodiment has been chosen to illustrate the invention, it will be understood by those skilled in the art that various changes and modifications can be made therein without departing from the scope of the invention as defined in the appended claims.

What is claimed is:

1. A corneal implant adapted to be received in a substantially circular corneal aperture and sutured thereto, the cornea having a thickness T, comprising:
   a substantially circular main body portion having anterior and posterior surfaces,
   said main body portion having a radially outwardly facing, substantially cylindrical peripheral surface with a height H greater than T and adapted to engage the edge forming the corneal aperture, said peripheral surface having a diameter substantially equal to the diameter of said anterior surface; and
   means, on said main body portion, for receiving sutures therethrough to couple said main body portion to the cornea,
   said peripheral surface extending posterior of said cornea when said implant is sutured to the cornea.

2. A corneal implant according to claim 1, wherein said main body portion comprises a convex portion and an annular ridge portion extending posterior of said convex portion.

3. A corneal implant according to claim 2, wherein said annular ridge has an annular posterior surface.

4. A corneal implant according to claim 2, wherein said annular ridge portion has a radially inwardly facing substantially cylindrical surface.

5. The corneal implant of claim 2, wherein said convex portion and said annular ridge portion are integrally formed.

6. A corneal implant according to claim 1, wherein said means comprises
   throughbores extending from the anterior surface of said main body portion to said peripheral surface, said throughbores having a diameter sufficient to accommodate suturing thread.

7. A corneal implant according to claim 6, wherein said main body portion includes from about 12 to about 24 throughbores.

8. A corneal implant according to claim 1, wherein said main body portion has a diameter of from about 5 mm. to about 10 mm.

9. A corneal implant according to claim 8, wherein said peripheral surface has a height of from about 1.1 mm. to about 1.5 mm.

10. A corneal implant according to claim 1, wherein said anterior surface of said main body portion is convex.

11. A corneal implant according to claim 10, wherein said posterior surface of said main body portion is concave.

12. A corneal implant according to claim 1, wherein said main body portion is formed of a polymeric material.

13. A corneal implant according to claim 12, wherein said polymeric material comprises methacrylate, silicone, polymethyl methacrylate, hydroxyethyl methacrylate, butyrate, a silicone-acrylate copolymer, a fluorocarbon, polypropylene, polyethylene terephthalate, stretched polytetrafluoroethylene having approximately nine billion randomly spaced microscopic pores per square inch, or a combination thereof.

14. A corneal implant according to claim 13, wherein said fluorocarbon is tetrafluoroethylene.

15. A corneal implant according to claim 12, wherein said polymeric material contains an ultraviolet chromophore.

16. A corneal implant adapted to be received in a substantially circular corneal aperture and sutured thereto, the cornea having a thickness T, comprising:
   a substantially circular main body portion having anterior and posterior surfaces,
   said main body portion having a radially outwardly facing, substantially cylindrical peripheral surface with a height H greater than T and adapted to engage the edge forming the corneal aperture; and
   means, on said main body portion, for receiving sutures therethrough to couple said main body portion to the cornea, said means comprising throughbores extending from the anterior surface of said main body portion to said peripheral surface, said throughbores having a diameter sufficient to accommodate suturing thread,
   said peripheral surface extending posterior of said cornea when said implant is sutured to the cornea.

17. A corneal implant according to claim 16, wherein said main body portion comprises a convex portion and an annular ridge portion extending posterior of said convex portion and
   said annular ridge has an annular posterior surface and a radially inwardly facing, substantially cylindrical surface.

18. A corneal implant according to claim 16, wherein said convex portion and said annular ridge portion are integrally formed.

19. A corneal implant according to claim 16, wherein said main body portion includes from about 12 to about 24 throughbores.

20. A corneal implant according to claim 16, wherein said main body portion has a diameter of from about 5 mm. to about 10 mm., and
   said peripheral surface has a height of from about 1.1 mm. to about 1.5 mm.

21. A corneal implant according to claim 16, wherein said anterior surface of said main body portion is convex, and
   said posterior surface of said main body portion is concave.

22. A corneal implant according to claim 16, wherein said main body portion is formed of a polymeric material.

23. A corneal implant adapted to be received in a substantially circular corneal aperture and sutured thereto, the cornea having a thickness T, comprising:
   a substantially circular main body portion having anterior and posterior surfaces,
   said main body portion having a radially outwardly facing, substantially cylindrical peripheral surface with a height H greater than T and adapted to engage the edge forming the corneal aperture; and
   means, in said main body portion, for receiving sutures therethrough to couple said main body portion to the cornea,
   said peripheral surface extending posterior of said cornea when said implant is sutured to the cornea.

24. A corneal implant according to claim 23, wherein said main body portion comprises a convex portion and an annular ridge portion extending posterior of said convex portion,
   said annular ridge has an annular posterior surface and a radially inwardly facing, substantially cylindrical surface, and
   said convex portion and said annular ridge portion are integrally formed.

25. A corneal implant according to claim 24, wherein said means comprises
 throughbores extending from the anterior surface of said main body portion to said peripheral surface, said throughbores having a diameter sufficient to accommodate suturing thread.
26. A corneal implant according to claim 25, wherein said main body portion includes from about 12 to about 24 throughbores,
said main body portion has a diameter of from about 5 mm. to about 10 mm., and
said peripheral surface has a height of from about 1.1 mm. to about 1.5 mm.

* * * * *